United States Patent [19]
Townsley et al.

[11] Patent Number: 5,567,325
[45] Date of Patent: Oct. 22, 1996

[54] THERMOPHILIC DIGESTION OF CHITIN-CONTAINING WASTE

[76] Inventors: Phillip M. Townsley; Peter J. Townsley, both of Unit No. 96, 2533 152nd Street, Surrey, British Columbia, Canada, V4P 1N4

[21] Appl. No.: 525,341

[22] Filed: Sep. 7, 1995

[51] Int. Cl.$^6$ ........................ C02F 3/02
[52] U.S. Cl. .................. 210/612; 210/620; 210/631; 210/919; 71/15
[58] Field of Search ................. 210/612, 613, 210/620, 630, 631, 919; 71/13, 16, 18, 14, 15

[56] References Cited

U.S. PATENT DOCUMENTS

| | | | |
|---|---|---|---|
| 3,711,392 | 1/1973 | Metzger et al. | 210/612 |
| 4,297,122 | 10/1981 | Wallace | 71/15 |
| 4,859,594 | 8/1989 | Portier | 210/601 |
| 5,141,646 | 8/1992 | Rozich | 210/631 |
| 5,208,159 | 5/1993 | Toda et al. | 435/252.1 |
| 5,374,627 | 12/1994 | Ito et al. | 514/55 |
| 5,431,819 | 7/1995 | Hack et al. | 210/631 |
| 5,492,624 | 2/1966 | Rozich | 210/613 |

OTHER PUBLICATIONS

Chemical Abstracts, pp. 1–17.

*Primary Examiner*—Thomas G. Wyse
*Attorney, Agent, or Firm*—Christensen O'Connor Johnson & Kindness PLLC

[57] ABSTRACT

Processes are provided for the thermophilic digestion (55° C. to 65° C.) of chitinous wastes to produce a solubilized form of chitin that may be applied to plants to stimulate their resistance to disease and attack by insects and fungi. Also provided are processes for treating a combined waste, including a waste containing chitin and an organic waste, to produce a substantially human and plant pathogen-fee product that may be used not only to stimulate plant resistance, but also to act as a fertilizer. The thermophilic digestion processes may be carried out with ubiquitous organisms, under at least marginally aerobic conditions, and preferably at a near-neutral pH.

20 Claims, 1 Drawing Sheet

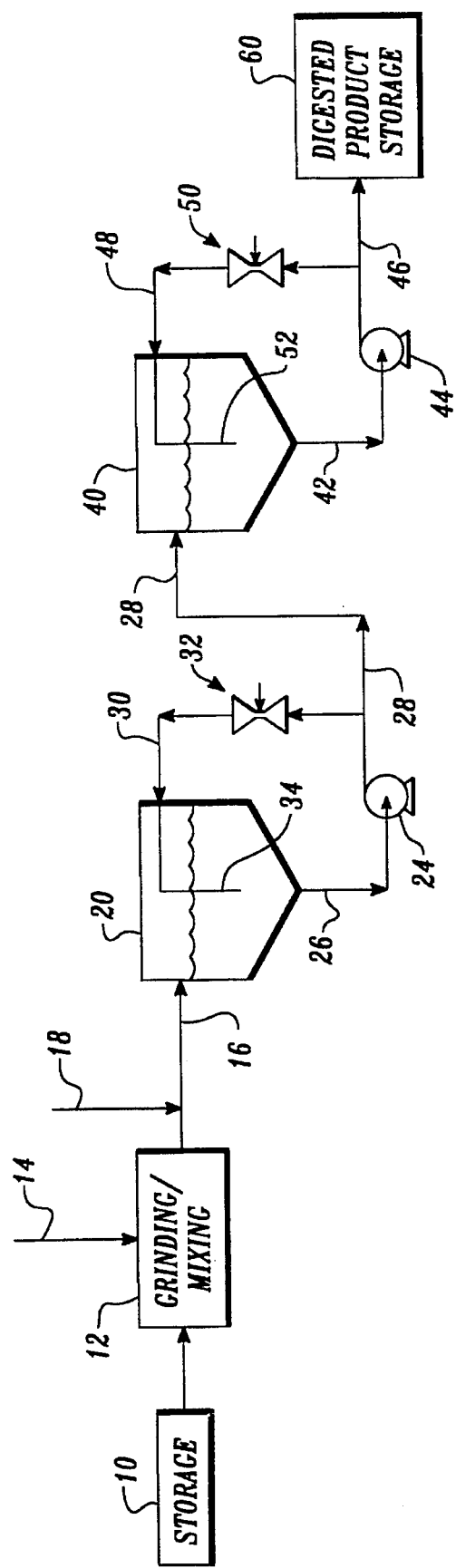

THERMOPHILIC DIGESTION OF CHITIN-CONTAINING WASTE

FIELD OF THE INVENTION

The invention relates to the thermophilic microbial digestion of a waste material to produce a useful product. More particularly, the invention provides a thermophilic bacterial digestion process for the conversion of chitin, obtained from waste material, into a solubilized disease-free form that is effective to stimulate the resistance of crops to diseases, and insect or fungal attack.

BACKGROUND OF THE INVENTION

During the processing of certain shellfish and crustacea, including shrimp, crabs, and lobster, as well as squid, a waste product containing bony, hard shell and beak pans is produced. These bony pans contain chitin and are largely disposed of as a waste product, typically in landfills. While this disposal method is commonplace, it is known that the waste has a high biological oxygen demand (BOD) and may contain pathogens harmful to human health such as strains of *E. coli*, salmonella, cholera, etc. Consequently, such disposal is not optimal, and may prove hazardous, if leachate from the waste seeps from the landfill into underground water supplies that may be used as a source of potable water.

in the past, attempts have been made to utilize waste containing chitin for agricultural purposes, and to extract chitin from the waste for use in medical applications. For example, an abstract of a published Japanese patent application, assigned Publication No. 03-228888, published on Oct. 9, 1991, describes the agricultural use of a mixture of (1) "the living bodies," skins, shells, residues of the processing of crustacea, insecta, and mollusks with (2) humus created by composting, animal wastes, food residues, and fish scrap at 70° C. or above. The abstract uses autotrophic soil bacteria, not heterotrophs such as Actymonyces, in the process. An autotroph is an organism that uses carbon dioxide as the sole carbon source. The soil bacteria are incorporated into the solid compost (72.6% moisture) mixture, along with a supply of air, to produce an organic fermented fertilizer containing chitosan components. It is alleged that chitosan enhances the stabilization of the fertilizer, causing agglomeration of the soil, thereby elevating water-holding properties and increasing the stability of microelements.

U.S. Pat. No. 5,374,627 relates to a composition containing 1 part by weight of chitosan hydrolyzate, having an average molecular weight in the range of 10,000 to 50,000, obtained by acid hydrolysis or enzymatic hydrolysis of chitosan, and 0.25 to 4 parts by weight of acetic acid, may be used to protect agricultural and horticultural plants from diseases and damage by certain pests. However, it is suggested that this composition may injure the plants. It is further suggested that any possible chemical injury to the plants may be reduced by admixing the composition with a deproteinized juice of alfalfa leaves.

U.S. Pat. No. 5,208,159 relates to the use of strains of chitinolytic bacteria, cultivated at temperatures between 20° C. and 40° C. to prepare a culture material from chitin or chitosan, which is usable directly as a solid antibacterial composition, or which may be fermented at the above mesophilic temperatures to produce such a solid antibacterial composition. Water may be added to the prepared culture material so that it may be used as an antibacterial, antinematode, and plant-cell activating composition.

The utilization of chitin-containing waste as a raw material for purified chitin for use in medical applications is limited relative to the total volume of the waste produced. In the process of producing purified chitin, chitin-containing waste is generally treated with hydrochloric acid to remove calcium and then washed with sodium hydroxide to remove residue or proteinaceous material to produce a semipurified chitin. When this semipurified form of chitin is treated with strong sodium hydroxide solution and heated for several hours, the chitin deacetylates to produce chitosan. This deacetylated form of chitin is useful in certain medical applications, as well as other applications, for example, as a flocculation chemical in waste water treatment.

There is a need for a method of converting chitin-containing waste on a large scale to a useful product to relieve pressure on landfills and to avoid health issues posed by the disposal of a waste containing, or capable of promoting the growth of, pathogenic microorganisms. Preferably, the process should be environmentally friendly, in the sense of not producing byproducts that are potentially hazardous to human health and that would pose a disposal problem. Moreover, process equipment should be relatively inexpensive, and operating costs should be relatively low so that a commercially viable product may be produced.

SUMMARY OF THE INVENTION

The invention provides a process for the commercial scale conversion of wastes containing chitin into soil amendments, and water-soluble compositions, that stimulate the resistance of agricultural and horticultural crops to disease, and attack by insects and fungi. The process of the invention subjects the chitin wastes to a thermophilic digestion process under controlled conditions resulting in the solubilization of the chitin so that it is free from potential human and plant disease carrying microorganisms and more readily available to plants to stimulate their immune systems and reactions.

According to the invention, a chitin waste, such as shrimp casings, crab and lobster shells, squid beaks, and the like, may be subjected to thermophilic digestion as an individual waste product, or it may be combined with another waste, such as animal fecal matter, lignocellulose, fish processing wastes, vegetable matter, and the like, and digested to produce a product that not only stimulates the resistance of plants, but also acts as a fertilizer. Moreover, the invention provides a continuous process, a batch process, and a semicontinuous process for the treatment of the chitin waste, either separately or in combination with another waste.

The continuous process for thermophilic bacterial digestion of chitin waste, or chitin waste combined with another waste, includes combining the chitin waste with sufficient liquid to make a pumpable mixture. This liquid may be water, or another waste that contains water. Moreover, in order to more readily digest the chitin, the waste may optionally be subjected to a comminution process to reduce the chitinous matter to a particle size distribution that is more readily digested. The pumpable mixture, containing the chitin waste, is then charged to a thermophilic digester. In the digester, the mixture is aerated at a rate sufficient to maintain aerobic or marginally aerobic conditions. The mixture is also subject to thermophilic digestion by microorganisms in the digester, resulting in the solubilization of the chitin. The digester is thermally insulated so that heat produced by the digestion process maintains the digester contents at a thermophilic temperature, usually without addition of external heat. In the continuous process of the invention, a volumetric portion of the digester contents containing solubilized chitin is continuously removed from the digester, while a similar volumetric portion of fresh mixture of chitin waste is charged to the digester.

In the semicontinuous process of the invention, a portion of the solubilized chitin is removed, at intermittent intervals, from the digester, and a similar volumetric portion of fresh chitin waste mixture is charged at intermittent intervals to the digester to maintain the volume of digester contents.

In the batch process of the invention, the pumpable mixture of waste containing chitin is charged to the thermophilic digester, and is aerated and subjected to thermophilic digestion for a time sufficient to solubilize a significant proportion of the chitin. When a predetermined conversion of chitin to solubilized chitin has occurred, the digested mixture is removed from the digester, filtered, and the soluble portion is available for use as a product that stimulates the resistance of plants to diseases and attack by insects and fungi, and also as a fertilizer, when chitin waste is treated in combination with an organic waste that is digestible to produce plant nutrients.

BRIEF DESCRIPTION OF THE DRAWINGS

FIG. 1 is a schematic process flow diagram of an embodiment of the invention.

DETAILED DESCRIPTION OF THE PREFERRED EMBODIMENTS

The invention provides a process for the conversion of chitin, contained in chitin waste products, into a solubilized or partially hydrolyzed, disease-free form of chitin. In one embodiment, the chitin-containing waste is subjected to the process of the invention as a separate waste product to produce a pathogen-free liquid product containing solubilized chitin that is useful to stimulate the resistance of plants to disease, and to attack by insects and fungi. In another embodiment, the chitin-containing waste is combined with an organic waste to produce a pathogen-free liquid product that is useful as both a fertilizer for plants, as well as a stimulant for plant resistance to disease and attack by insects and fungi. In the process of the invention, the chitin-containing waste undergoes thermophilic digestion, under at least marginally aerobic conditions, to produce a substantially pathogen-free product.

In the specification and claims, a "thermophilic digestion process" means a process whereby microorganisms metabolize a substrate, such as organic waste, including chitin, at a temperature in the thermophilic range, from about 55° C to about 80° C., under aerobic or marginally aerobic conditions. Preferably, temperature is maintained in the thermophilic range, under normal ambient temperature conditions, without addition of heat but by exothermic heat of digestion conserved through thermal insulation of the digester. However, under certain circumstances, such as at startup or under severe ambient temperatures exceeding the capability of digester heat insulation to retain process temperatures, external heat may be added. The microorganisms utilized may be of ubiquitous varieties of thermophilic bacteria and preferably include thermophilic chitinolytic bacteria. While the process is carded out under aerobic conditions, it may also be carried out under close to anaerobic conditions, also termed "marginally aerobic conditions" where the level of dissolved oxygen may be as low as 0.02 mg/l. Preferably, dissolved oxygen is maintained in the range of about 0.1 mg/l to about 5 mg/l. A process for thermophilic digestion of certain organic wastes is disclosed in U.S. Pat. No. 4,292,328, which is hereby incorporated by reference, to the extent consistent with the present invention.

The term "solubilized chitin" means any water-soluble end product of the biological degradation of chitin that stimulates the resistance of plants to disease, and attacks by insects and fungi.

The terms "waste containing chitinous material," "chitin waste," and "chitin-containing waste" refer to waste that contains material containing chitin, such as shrimp casings, lobster and crab shells, squid beaks, insect exoskeletons, and the like.

The term "organic waste" refers to a waste that contains organic compositions that are biodegradable by microorganisms under thermophilic digestion conditions.

The term "normal ambient conditions of temperature" refers to ambient temperatures at which thermophilic conditions may be maintained in a digester that is heat insulated to prevent excessive heat loss, without addition of external heat. Typically, normal ambient temperatures are above about 10° C., without excessive heat insulation of the digester.

A waste containing chitin may be obtained from a variety of sources, usually from a fish, shellfish, squid, and crustacea processing facility. The waste is preferably stored to provide an inventory for use as a continuous supply of raw material in the process of the invention. In certain instances, it may be advantageous to subject the chitin waste to a comminution, or grinding, process to reduce the size of solid chitin-containing parts of the waste to a size distribution that facilitates thermophilic digestion. Smaller particles, having a larger surface area to volume ratio, are more readily attacked by microorganisms so that they are more rapidly biodegraded and the chitin solubilized. Often, the chitin-containing waste is already in a suitably shredded or comminuted form as a result of processes carded out by the fish processor. Preferably, the chitin-containing waste has a particle size in the range from about 5 mm to about 20 mm.

To facilitate handling of the chitin-containing waste in a chemical processing system, the waste is preferably in a pumpable form. However, in certain instances, it may be preferable to maintain the chitin waste in solid form and subsequently mix the solids into a liquid organic waste, thereby increasing the biodegradable fraction of the liquid waste.

To render the chitin-containing waste pumpable, the waste may be ground in a "grinder pump", with the addition of a small quantity of water, or a liquid organic waste. Such pumps include an internal mechanism for grinding while pumping and are commercially available. The amount of liquid added should be sufficient to render the waste mixture pumpable while maintaining a sufficiently high concentration of biodegradable organic matter to allow thermophilic conditions to develop during digestion. The chitin waste may alternatively be added to a mixing vessel supplied with a high speed agitator capable of reducing the size of chitin waste parts to within a desired size range. Chitin waste may also alternatively be added directly into the digester, for example by a screw-type conveyor, provided that mixing within the digester is adequate to suspend or mix the suspension, and to reduce chitin waste size, if required.

In those embodiments of the invention where the chitin-containing waste is combined with another organic waste, the mixing may be performed, as above-described in a mixing vessel, or grinder, or otherwise. Preferably, the organic waste is a liquid waste so that the addition of water is minimized. Preferably, the resultant mixture contains up to about 10 wt % (dry weight) solids, more preferably about 4 wt % to about 5 wt %, based on the dry weight of chitin as a fraction of the total weight of the mixture. Most preferably, the mixture contains about 1 wt % chitin. In the embodiments in which the chitin waste is not combined with another waste, the chitin is mixed with water, as described above, to provide a medium containing from about 1 to about 8 wt % chitin, preferably not more than about 6 wt % chitin.

The chitin-containing waste is then pumped to a thermophilic digester. The digester is preferably a thermally insulated vessel supplied with an apparatus for aerating its contents. In the batch process of the invention, the digester may be of substantially cylindrical shape, supplied with a conical bottom for ease of withdrawal of product. A feed stream, including the chitin waste, is charged to a top portion of the digester. Preferably, the digester is aerated by removing a portion of the contents of the digester into the suction of a pump, and pumping this portion back into the digester through a conduit supplied with a venturi that is controlled to draw air, under suction, into the pumped digester medium in the conduit. The aerated medium is preferably debouched back into the digester below the surface of the digester medium in the digester. The rate of aeration is controlled by the rate of pumping and air pressure drop at the venturi. Preferably, aeration is controlled to maintain a dissolved oxygen content of from about 0.1 to about 5 mg/l in the digester medium. This provides an aerobic, or "marginally aerobic" environment, most suitable for rapid growth of thermophilic microorganisms for biodegrading chitin waste to produce soluble chitin, and also for digesting any biodegradable organic wastes.

In a batch system, the digester is initially at ambient temperature. However, after aeration for several hours in the presence of ubiquitous thermophilic bacteria, or other thermophilic bacteria doped into the digester, the temperature of the medium in the digester rises as a result of exothermic heat of digestion. The rate of temperature increase is dependent upon several factors, including the rate of aeration, the types of thermophilic bacteria present and their respective growth rates, the proportion of biodegradable solids in the waste, and the effectiveness of thermal insulation of the digester in preventing heat loss. However, once a temperature of 55° C. has been achieved, the process is "thermophilic". Preferably, the process of the invention is carried out in a temperature range where the lower end of this range is sufficient to provide a pasteurized product, while the upper end of the range is not so high as to inhibit the activity of microorganisms in biodegrading chitin waste or organic waste. Preferably, the temperature is in the range 55° to 65° C. Thermophilic digestion is carried out for a period sufficient to convert a predetermined amount of chitin to solubilized chitin. This time period will vary based on numerous factors, including the nature of the waste being digested, digestion temperature, waste concentration, and desired level of chitin conversion. Typically, the thermophilic digestion process is carried out for from about 24 to about 72 hours at 55° to 65° C., sufficient to convert from about 50 to about 80% of the chitin to soluble chitin. However, the process may proceed for longer or shorter periods, depending upon the degree of chitin conversion desired.

The aeration rate of the digester is important. On the one hand, the aeration rate should be sufficient to maintain at least marginally aerobic conditions within the digester. On the other hand, an oversupply of air removes heat from the digester in exiting air, an undesirable condition. Thus, aeration rate is dictated by both the level of dissolved oxygen in the digester medium, as well as the required temperature. If ambient temperature conditions drop to such a low level that thermophilic temperature conditions can no longer be maintained in the digester, then external heat should be supplied and aeration rate maintained to preserve at least marginally aerobic conditions. External heat may be supplied through heating coils inside the digester or heating of the recirculation aerator conduit. Aeration also serves to agitate digester contents due to the release of air bubbles into the liquid medium. Preferably, the air is sparged into the medium below its upper surface. More preferably, a pump-around system including an aerating venturi, as described above, is used.

Preferably, the pH of the digestion process is controlled to a near-neutral pH level. As digestion proceeds, pH tends to increase due to digestion product formation. Such pH elevation tends to deactivate thermophilic microorganisms, thereby reducing the rate of thermophilic digestion. Most preferably, pH is controlled to the range from about 6.5 to about 7.5, as discussed in more detail below.

When the desired level of chitin conversion has been obtained, the digested product is removed from the digester to product storage. This product, substantially free of pathogens, may then be applied to plants, such as agricultural and horticultural crops, to stimulate resistance to disease, and attack by insects and fungi. Also, when the product includes biodegraded organic waste matter, then it serves as a useful source of plant nutrients.

A preferred embodiment of the invention, a continuous process utilizing a series of continuously stirred mixing vessels in series, is schematically illustrated in FIG. 1, to which reference is made to facilitate description. Chitin-containing waste is collected from various sources and placed in a storage tank 10. In a continuous process, it is preferred that the chitin waste be in a pumpable form. Waste is charged to a mixing vessel for combining with a liquid, either water or an organic waste 14, and optional grinding, if it is desirable to further contribute chitinous material into smaller sizes. As illustrated, further organic waste 18 may be added to effluent 16 from the mixing and optional grinding steps. The combined waste in conduit 16 is charged to the digester 20. Digestion medium withdrawn from digester 20 in conduit 26 enters the suction of pump 24 and is pumped through conduit 30, containing an aerating venturi 32, into vertical downpipe 34 extending below the surface of the digestion medium for return as an aerated medium to the digester. Venturi 32, located in conduit 30, controlledly draws air into the conduit and aerates the medium flowing in the conduit. Consequently, downpipe 34 debouches an aerated mixture into the digester. By suitably controlling the rate of air entering the venturi, and the rate of medium pumped in conduit 30, the dissolved oxygen content of medium in digester 20 may be controlled at a desired level.

FIG. 1 illustrates a two-stage continuous system wherein effluent from the first digester 20 is controlledly supplied in conduit 28 to a second digester 40. As shown, medium from digester 40 is withdrawn in conduit 42 and enters the suction of pump 44. The pump discharges a proportion of the medium through conduit 48, containing an aerating venturi 50, into a vertical downpipe 52 to below the surface of the medium in digester 40. Another portion of the medium is routed through conduit 46 to digested product storage 60.

As pointed out above, since the digestion is carried out under thermophilic conditions, the digested product is substantially pathogen-free and may be used to treat plants, either to stimulate resistance to diseases, and attack by insects and fungi, or to also provide plant nutrients, when the chitin waste was combined with a biodegradable organic waste.

Clearly, the process illustrated in FIG. 1 may be used in either a continuous or semicontinuous mode of operation, as well as a batch mode. In the continuous mode, charge may be continuously supplied through conduit 16 to digester 20 while product is withdrawn continuously through conduit 46 to product storage. In the semicontinuous mode, the charge may be supplied intermittently. When the charge is supplied intermittently, then product is also preferably withdrawn intermittently in order to maintain the volume of medium in the system subject to thermophilic digestion.

During steady-state operation, the media in digesters 20 and 40 are maintained at thermophilic temperatures, due to release of exothermic heat of digestion, and insulation of the digesters to prevent excessive heat loss. However, during startup, the digesters may be at ambient temperatures. Under these circumstances, external heat may be supplied to the digesters in order to promote rapid microbial growth to more quickly achieve a thermal steady state. Alternatively, the digesters may be aerated, as explained above, to allow microbial proliferation until there is sufficient biological activity that exothermic heat elevates the temperatures of the digesters to the thermophilic range. In the event that heat is supplied from an external source, then this heat may be supplied through low-pressure steam coils within the digester, or other means. External heat may also have to be supplied when ambient temperatures drop to such low levels that heat losses from the digesters prevent the maintaining of thermophilic conditions.

The pH of the waste medium subject to thermophilic digestion is important. Preferably, the pH is maintained in a near-neutral range to maximize the rate of biological activity. More preferably, the pH is maintained in the range from about 6.5 to about 7.5. However, during the thermophilic digestion process, pH of the waste tends to increase. This increase in pH reduces biological activity and thereby also reduces the rate of conversion of chitinous waste to solubilized chitin, and the rate of conversion of any organic waste to digestion products. Thus, control of pH is important to maintain digestion rate. Preferably, the pH is adjusted downward to the near-neutral range by the addition of predetermined quantities of an acid, such as sulfuric acid. More preferably, the pH may be adjusted by the addition of a predetermined quantity of a greasy waste, such as a waste containing vegetable oils, animal fats, or both. These greasy wastes, when added to the digestion medium, undergo thermophilic digestion to produce fatty acids and other metabolic products that neutralize other digested products that caused the increase in pH. As a result, addition of predetermined quantities of greasy wastes, either continuously or intermittently, may be used to control pH to any desired range. Preferably, pH is continuously monitored using pH probes and greasy waste is charged continuously in response to detected pH changes, allowing for a lag time to permit digestion of previously added greasy waste. Thus, an excursion of pH from a control point would lead to an injection of a predetermined amount of greasy waste, taking into account any undigested prior added greasy waste.

The following example illustrates aspects of the invention and does not define or limit the scope of the invention, as described above and claimed herebelow.

EXAMPLE

Squid waste is obtained from a waste-processing plant. This waste, comprising about 31% of the squid, contains the stomach, liver, gonad, ink sac, gut, head and chitinous pen tissue of the squid. Under normal conditions, this waste will degrade very rapidly and become extremely malodorous. Therefore, it must be removed from the fishery area as soon as possible. The moisture content of the waste is greater than about 80%.

In accordance with the invention, this crude waste is fed directly to a digester through a grinder pump to reduce the size of the waste. In a batch digestion process of the invention, the waste in the digester reaches thermophilic temperatures, i.e., temperatures greater than about 55° C., within about 48 hours of adding ubiquitous microorganisms. Digestion at thermophilic temperatures then proceeds for several days to ensure liquefaction of most of the solids, and total pasteurization. The resultant pathogen-free liquid waste is then used as a fertilizer, or to stimulate resistance of crops to diseases and insect or fungal attack, or for both purposes.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A continuous process for thermophilic bacterial digestion of an aqueous waste including chitin-containing matter, the process comprising:

(a) combining a waste containing chitinous material with sufficient water to make a pumpable mixture and to maintain the concentration of digestible waste constituents of the mixture at a level sufficient to allow the temperature of the mixture to be maintained at a thermophilic temperature during thermophilic digestion of the mixture under normal ambient conditions without addition of external heat;

(b) charging the mixture to a thermophilic digester to commingle with medium in the digester;

(c) aerating a medium in the digester at a rate sufficient to maintain the medium under at least marginally aerobic conditions;

(d) subjecting the medium to thermophilic digestion in the digester by microorganisms, while aerating, to solubilize at least a portion of the chitin of the chitinous waste; and (e) continuously removing a volume of digested medium containing solubilized chitin from the digester, and continuously charging a substantially equal volume of pumpable mixture to the digester.

2. The process of claim 1, wherein the step of combining comprises mixing with water and an organic waste selected from the group consisting of animal fecal matter, fish processing waste, lignocellulose, slaughterhouse waste and vegetable matter.

3. The process of claim 1, wherein the step of combining includes comminuting the chitinous material of the waste to a particulate size distribution that facilitates thermophilic digestion to produce solubilized chitin.

4. The process of claim 1, wherein the step of combining includes combining with sufficient water to make a mixture comprising from about 10 wt % to about 20 wt % biodegradable solids, and about 1 wt % chitin.

5. The process of claim 1, wherein the aerating is with air at a rate sufficient to produce a dissolved oxygen content above 0.02 mg/l in the mixture in the digester.

6. The process of claim 1, wherein the subjecting of the medium to thermophilic digestion includes thermophilic digestion at a temperature in the range from about 55° to about 65° C.

7. The process of claim 1, wherein the subjecting of the medium to thermophilic digestion includes monitoring the pH of the mixture in the digester, and adjusting the pH to the range from about 6.5 to about 7.5.

8. The process of claim 7, wherein the adjusting of the pH comprises adding a waste selected from the group consisting of vegetable oils and animal fats to the digester.

9. The process of claim 7, wherein the adjusting of the pH is by the addition of ammonia.

10. A process for thermophilic bacterial digestion of an aqueous waste including chitin-containing matter, the process comprising:

(a) combining a waste containing chitin with sufficient water to make an aqueous pumpable mixture and to maintain the concentration of digestible constituents of the waste at a level sufficient to allow the temperature of the mixture to be maintained in a thermophilic range of temperatures during thermophilic digestion of the mixture, under normal ambient temperature conditions;

(b) charging the mixture to a thermophilic digester;

(c) aerating the mixture in the digester at a rate sufficient to maintain the mixture under at least marginally aerobic conditions;

(d) subjecting the mixture to thermophilic digestion for a time sufficient to solubilize a predetermined proportion of the chitin and produce a digested waste product substantially free of pathogens; and (e) removing the digested waste product from the digester.

11. The process of claim 10, wherein the combining with water further comprises mixing with an organic waste selected from the group consisting of animal fecal matter, fish processing waste, lignocellulose, slaughterhouse waste and vegetable matter.

12. The process of claim 10, wherein the step of combining includes comminuting the chitin of the waste to a particulate size distribution that facilitates thermophilic digestion to produce solubilized chitin.

13. The process of claim 10, wherein the step of combining includes combining with sufficient water to make a mixture comprising from about 10 wt % to about 20 wt % solids, and about 1 wt % chitin.

14. The process of claim 10, wherein the aerating is with air at a rate sufficient to produce a dissolved oxygen content above about 0.2 mg/l in the mixture in the digester.

15. The process of claim 10, wherein the subjecting of the mixture to thermophilic digestion includes thermophilic digestion at a temperature in the range from about 55° to about 65° C.

16. The process of claim 10, wherein the subjecting of the mixture to thermophilic digestion includes monitoring the pH of the mixture in the digester, and adjusting the pH to the range from about 6.5 to about 7.5.

17. The process of claim 16, wherein the adjusting of the pH comprises adding a waste selected from the group consisting of vegetable oils and animal fats.

18. The process of claim 16, wherein adjusting of the pH is by the addition of ammonia.

19. A process for thermophilic bacterial digestion of an aqueous waste including chitin-containing matter, the process comprising:

(a) combining a waste containing chitin with liquid waste to produce a mixture comprising from about 10 wt % to about 20 wt % biodegradable solids, and up to about 1 wt % chitin;

(b) subjecting the mixture to bacterial thermophilic digestion at a temperature in the range of from about 55° to about 65° C., while aerating the mixture at a rate sufficient to maintain a dissolved oxygen content of about 0.2 mg/l, and maintaining the pH of the mixture in the range from about 6.5 to about 7.5, to solubilize at least a portion of the chitin; and (c) producing a substantially pathogen-free digested liquid product containing solubilized chitin.

20. The process of claim 19, further comprising applying the digested liquid product to plants.

* * * * *

UNITED STATES PATENT AND TRADEMARK OFFICE
CERTIFICATE OF CORRECTION

PATENT NO. : 5,567,325
DATED : October 22, 1996
INVENTOR(S) : P.M. Townsley et al.

It is certified that error appears in the above-indentified patent and that said Letters Patent is hereby corrected as shown below:

| COLUMN | LINE | |
|---|---|---|
| 8 | 63 | After "above" insert --about-- |

Signed and Sealed this

Fifth Day of August, 1997

Attest:

Attesting Officer

BRUCE LEHMAN

Commissioner of Patents and Trademarks